US000001198H

United States Statutory Invention Registration [19]

[11] Reg. Number: H1198

Larrick et al.

[43] Published: Jun. 1, 1993

[54] *PSEUDOMONAS AERUGINOSA* TYPE-SPECIFIC HUMAN MONOCLONAL ANTIBODIES, THEIR PREPARATION AND USE

[75] Inventors: James W. Larrick, Woodside, Calif.; Andrew A. Raubitschek, Bethesda, Md.

[73] Assignee: Cetus Corporation, Emeryville, Calif.

[21] Appl. No.: 727,515

[22] Filed: Apr. 26, 1985

[51] Int. Cl.[5] ..... C07K 15/28; C12N 5/24; C12N 5/28

[52] U.S. Cl. ..... 530/388.4; 935/96; 935/100; 435/70.21; 435/240.27

[58] Field of Search ..... 435/68, 172.2, 240; 424/85, 177, 87; 935/95, 99, 100, 96, 107

[56] References Cited

U.S. PATENT DOCUMENTS

| | | | |
|---|---|---|---|
| 4,434,230 | 2/1984 | Ritts, Jr. | 435/240 |
| 4,451,570 | 5/1984 | Royston et al. | 435/240 |
| 4,464,465 | 8/1984 | Lostrom | 435/68 |
| 4,529,694 | 7/1985 | Lazarus et al. | 435/68 |

FOREIGN PATENT DOCUMENTS

| | | | |
|---|---|---|---|
| 0062409 | 10/1982 | European Pat. Off. | 435/240 |
| 0101039 | 2/1984 | European Pat. Off. . | |
| 8501659 | 4/1985 | PCT Int'l Appl. . | |
| 2113715 | 8/1983 | United Kingdom | 435/240 |

OTHER PUBLICATIONS

Olsson, L. et al., P.N.A.S. 77(9):5429–5431 (Sep. 1980).
Cote, R. J. et al., Proc. Natl. Acad. Sci., USA 80:2026–2030 (Apr. 1983).
Darveau, R. P. et al., J. Bacteriology, 155(2):831–838 (Aug. 1983).
Teng, N. H. et al., Proc. Natl. Acad. Sci., USA, 80:7308–7312 (Dec. 1983).
Cryz et al., *Inf. Imm.* (1983) 40:659–664.
Moody et al., *Infect. Imm.* (1978) 21:905–913.
Kohler and White, *J. Infect. Dis.* (1977) 136: 112–116.
Collins et al., *J. of Trauma* (1983) 23: 530–534.
Cryz et al., *Infect. Immun.* (1983) 39: 1072–1079.
Sawada et al., *J. Infect. Dis.* (1984) 150: 570–576.
Hancock et al., Infect. Immun. (1982) 37: 166–171.
Mackie et al., *J. Immunol.* (1982) 129: 829–32.
Fisher, M. W. (1977) *J. Infect. Dis.* 136, S181–S185.
Apicella, M. A. et al., *Biological Abstracts,* vol. 73, 1982, ref. 83064, *Infect. Immun.* 34 (3), pp. 751–756 (1981).
Morse, S. A. et al., *Biological Abstracts,* vol. 74, 1982, ref. 61778 *J. Infect. Dis.* 145 (2) 206–216, 1982.
Hancock, R. E. W. et al., *Biological Abstracts,* vol. 75, 1983, ref. 10652 *Infect. Immun.* 37 (1):166–171, 1982.
Mutharia et al. (1984) *Infect. Immun.* 45 (3), 631–6.

*Primary Examiner*—Robert L. Stoll
*Assistant Examiner*—John M. Covert
*Attorney, Agent, or Firm*—Albert P. Halluin

[57] ABSTRACT

Serotype-specific human anti-*Pseudomonas* monoclonal antibodies which bind to determinants of the cell wall lipopolysaccharides of *P. aeruginosa* are prepared from hybrid cell lines. The antibodies may be of any isotype. These antibodies may be used to treat infections caused by *P. aeruginosa.*

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

*PSEUDOMONAS AERUGINOSA* TYPE-SPECIFIC HUMAN MONOCLONAL ANTIBODIES, THEIR PREPARATION AND USE

BACKGROUND OF THE INVENTION

This invention relates to the production of human antibodies which are type specific and directed against *Pseudomonas aeruginosa.*

*Pseudomonas aeruginosa* is a highly virulent pathogen which infects patients receiving immunosuppressive therapy or suffering from severe thermal burns or other serious injuries, cystic fibrosis, or neoplastic diseases. Mortality from *P. aeruginosa* has been reduced as the result of such therapeutic agents as mafenide acetate and silver salts which inhibit bacterial colonization of the burn wound surface, potent antibiotics for treating bacteremia, and barrier isolation to minimize contact of the patient with hospital flora. Such agents, however, have only proved partially successful in controlling the morbidity and mortality associated with *Pseudomonas* infections.

Recently, researchers have found that specific antibodies constitute a critical immunologic defense mechanism against *Pseudomonas* disease; therefore, vaccines have been administered to patients in attempts to increase antibody titers in the patients. No non-toxic vaccines have been found to date which are particularly effective against the pathogen.

It is not yet clear what components of *P. aeruginosa* are responsible for its virulence. Many different types of infections are recognized, from acute localized eye infections and chronic lung infections to generalized systemic infections and septicemia. Several lines of evidence, however, suggest that lipopolysaccharide (endotoxin) (LPS) contributes substantially as a pathogenic factor. These include the toxic nature of *P. aeruginosa* LPS (Pennington et al., *Am. J. Med.,* 58, 629–636 (1975)), and the fact that circulating D antibodies to LPS are shown to prevent or attenuate some of the adverse effects of LPS in experimental models (Cryz et al., *Infect. Immun.,* 40, 659–664 (1983); Young et al., *J. Clin. Invest.,* 56, 850–861 (1975)). Pollack et al., *J. Clin. Invest.,* 63, 276–286 (1979) concluded from their studies that serum antibodies to LPS found in most patients with *P. aeruginosa* septicemia were correlated with patient recovery.

Numerous studies have indicated that immunoglobulin G (IgG) antibody to LPS is protective in experimentally infected animals (Cryz et al., supra; Moody et al., *Infect. Immun.,* 21, 905–913 (1978)), and more so when combined with an antibiotic (Cryz et al., supra). A heptavalent vaccine containing LPS of the seven Fisher-Devlin-Gnabasik immunotypes of *P. aeruginosa* (Fisher et al., *J. Bacteriol.,* 98, 833–836 (1969)) was found to be effective in inducing antibodies in humans. See Kohler and White, *J. Infect. Dis.,* 136, 112–116 (1977). Attempts to immunize patients at high risk of *P. aeruginosa* infection with this vaccine, however, have been only moderately successful due in part to the potent endotoxin activity of LPS. Local and systemic adverse reactions to endotoxin, including fever, malaise, and pain at the site of injection, can limit vaccine dosage. See Pennington et al., supra.

Collins et al., *J. of Trauma,* 23, 530–534 (1983) disclose a test of a commercially available human IgG in burned mice for activity against the seven immunotypes of *P. aeruginosa* and an additional strain. The human IgG was not effective against immunotypes 5 and 6 but was protective against immunotypes 1-4 and 7. In addition, Cryz et al., *Infect. Immun.,* 39, 1072 (1983) and Sawada et al., *J. Infect. Dis.,* 150, 570 (1984) disclose work suggesting that type-specific anti-*P. aeruginosa* antisera and mouse monoclonal antibodies can reduce the lethality of these bacteria in the burned mouse model. Hancock et al., *Infect. Immun.,* 37, 166–71 (1982), Mackie et al., *J. Immunol.,* 129, 829–32 (1982) and EP 101,039 also disclose monoclonal antibodies against *P. aeruginosa.*

There is a need to develop human monoclonal antibodies for passive immunotherapy of patients infected with *P. aeruginosa.*

SUMMARY OF THE INVENTION

Accordingly, the present invention provides a serotype-specific human anti-*Pseudomonas* antibody which binds to determinants of the cell wall lipopolysaccharides of *Pseudomonas aeruginosa* and whose population is substantially homogeneous, i.e., the antibody is monoclonal.

Another aspect of the invention herein is a stable, permanent hybrid cell line which produces such antibody and progeny of the cell line.

In addition, the invention relates to compositions for treating infections caused by *Pseudomonas aeruginosa* comprising a therapeutically effective amount of such antibody in association with a pharmaceutically acceptable parenteral vehicle.

In a further aspect, the invention relates to a method for treating a mammalian patient for infections caused by *P. aeruginosa* comprising administering an effective amount of such antibody to the patient parenterally.

The antibodies herein may be successfully utilized for passive immunotherapy against, or prophylaxis of, *Pseudomonas* infections.

DESCRIPTION OF THE PREFERRED EMBODIMENTS

As used herein the term "cell line" refers to individual cells, harvested cells, and cultures containing cells so long as they are derived from cells of the cell line referred to.

As used herein with respect to hybrid cell lines, the term "progeny" is intended to include all derivatives, issue, and offspring of the cell lines regardless of generation of karyotypic identity.

As used herein with respect to a given antibody, the term "functional equivalent" means an antibody that recognizes the same determinant as and crossblocks the antibody referred to. It is intended to include antibodies of the same or different immunoglobin class and antigen binding fragments (e.g., Fab, $F(ab')_2$, Fv) of the antibody.

As used herein with respect to administering antibody to patients, the term "treat" and conjugates thereof refers to therapy and/or prophylaxis.

As used herein the term "monoclonal antibody" refers to an antibody selected from antibodies whose population is substantially homogeneous, i.e., the individuals of the antibody population are identical except for naturally occurring mutations.

As used herein with respect to characterizing the claimed hybrid cell lines, the terms "permanent" and "stable" mean that the lines remain viable over a prolonged period of time, typically at least about six months, and maintain the ability to produce the specified monoclonal antibody through at least about 50 passages.

As used herein the term "serotype" refers to one of the seven Fisher-Devlin-Gnabasik immunotypes of *P. aeruginosa* described by Fisher et al., *J. Bacteriol.*, 98, 833–836 (1969).

The human antibodies herein which are specific against one or more of the seven serotypes are monoclonal. While it is preferably to have an antibody against all seven serotypes, exemplified herein are antibodies directed against serotypes 3 and 7 and against serotype 4. Also, the antibodies herein may be any isotype, preferably IgM or IgG. They are made by fusion involving cells of human origin. The human embodiments may be the products of hybridomas synthesized by somatic cell hybridization using a mouse or human myeloma cell line or a mouse×human parent hybrid cell line and a human cell line producing sufficiently high levels of anti-*P. aeruginosa* serotype-specific antibodies. The latter cell line may be from, e.g., peripheral blood lymphocytes (PBL) or splenocytes, with PBL being exemplified, and are transformed with Epstein-Barr virus (EBV) as described, for example, by Foung, et al., *J. Immunol. Methods*, 70, 83–90 (1984). The latter cell line may be obtained from non-immunized volunteers screened for or known to produce high serum anti-*P. aeruginosa* serotype-specific titers of IgM, IgG and/or IgA.

When transformation is employed, the most successful approaches have been either to pre-select the population of B cells to be transformed or to post-select the antigen-specific transformed populations by panning or rosetting techniques, as described by Kozbar et al., *Scan. J. Immunol.*, 10, 187–194 (1979) and Steinitz et al., *J. Clin. Lab. Immun.*, 2, 1–7 (1979). Recently EBV transformation has been combined with cell fusion to generate human monoclonal antibodies (see, e.g., Foung et al., *J. Immun. Meth.*, 70, 83–90 (1984)), due to instability of immunoglobulin secretion by the EBV transformed lines, increased immunoglobulin secretion by hybridomas when compared to EBV lymphoblastoid cell lines, and higher frequencies of rescue of the antigen-specific populations.

EBV most frequently infects and transforms IgM-bearing B cells, but B cells secreting other classes of Ig can also be made into long-term lines using the EBV fusion technique, as described by Brown and Miller, *J. Immunol.*, 128, 24–29 (1982).

One strategy for preparing and identifying hybrids which produce antibodies of the invention follows. Peripheral blood cells are obtained from cystic fibrosis patients chronically colonized with *P. aeruginosa* and known to have substantial titers of anti-*P. aeruginosa* serotype-specific antibodies. Lymphocytes are transformed with Epstein-Barr virus and the lymphoblastoid cell lines are screened on a heptavalent vaccine containing all seven *P. aeruginosa* serotypes by ELISA. The positive cell lines are then fused to a fusion partner consisting of a mouse×human B cell hybrid resistant to ouabain and 6-thioguanine by the technique described by Truitt et al. in *Monoclonal Antibodies and Functional Cell Lines* (ed. by R. H. Kennett et al.), Plenum, N.Y.: 1984. In the selection medium ouabain is used to kill unfused EBV transformants, and hypoxanthine and azaserine are used to kill unfused mouse x human fusion partner. Supernatants from the selected growing hybrid cells are screened by ELISA against bacteria from each serotype. Hybrids which are positive for at least one serotype are expanded. Cells from these positive hybrids are subcloned and used to produce monoclonal antibodies, which are evaluated for their antigen-binding and physicochemical properties.

The antigen-binding ability of the antibodies herein is evaluated by LPS immunoblots, ELISAs and bacterial binding. Those antibodies which have the ability to block the adverse biological effects of *P. aeruginosa* in mammals regardless of the mechanism involved are preferred.

The hybridomas which produce the antibodies of this invention may be grown in suitable culture media such as Iscove's media or RPMI-1640 medium from Gibco, Grand Island, N.Y., or in vivo in immunodeficient laboratory animals. If desired, the antibody may be separated from the culture medium or body fluid, as the case may be, by conventional techniques such as ammonium sulfate precipitation, hydroxylapatite chromatography, ion exchange chromatography, affinity chromatography, electrophoresis, microfiltration, and ultracentrifugation.

The antibodies of this invention may be used passively to immunize individuals who suffer from *P. aeruginosa* septicemia or are at risk with respect to *P. aeruginosa* infection. Patients at risk include those receiving immunosuppressive therapy and those suffering from severe thermal burns or other serious injuries, cystic fibrosis and cancer.

Preferably, at least two different antibodies, each of which recognizes and binds to a distinct serotype, are employed.

In addition, a combination of antibiotic and one or more serotype-specific antibodies may be employed. Also, one or more type-specific human monoclonal antibodies herein may be used in combination with one or more antibodies (preferably human monoclonal antibodies) directed against the exotoxin A portion of *P. aeruginosa*. The antibodies may act synergistically in that the type-specific antibody may kill the organism and/or hasten its clearance while the exotoxin A specific antibody may neutralize the toxin. The exotoxin A specific antibodies may be prepared using the procedure described herein where the immunizing agent is exotoxin A or where patients with high anti-exotoxin A titers are screened by an exotoxin A ELISA. The procedure is more fully described in copending U.S. application Ser. No. 727,514 entitled "*Pseudomonas aeruginosa* Exotoxin A Monoclonal Antibodies, Their Preparation and Use" to James Larrick et al. filed Apr. 26, 1985, now U.S. Pat. No. 4,677,070.

The antibodies may be administered to the patient by any suitable technique, including subcutaneous and parenteral administration, preferably parenteral. Examples of parenteral administration include intravenous, intraarterial, intramuscular and intraperitoneal, preferably intravenous. The dose and dosage regimen will depend mainly upon whether the antibody/antibodies is/are being administered for therapeutic or prophylactic purposes, the patient, and the patient's history. The total pharmaceutically effective amount of an antibody administered per dose will typically be in the range of about 0.2 to 20 mg/kg of patient body weight.

For parenteral administration the antibody/antibodies will generally be formulated in a unit dosage injectable form (solution, suspension, emulsion) in association with a pharmaceutically acceptable parenteral vehicle. Such vehicles are inherently nontoxic and nontherapeutic. Examples of such vehicles include water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances which enhance isotonicity and chemical stability, e.g., buffers and preservatives. The antibody will typically be formulated in such vehicles at a concentration of about 0.1 mg/ml to 100 mg/ml.

The various aspects of the invention are further described by the following examples, which are not intended to limit the invention in any manner. In these examples all percentages for solids are by weight and all percentages for liquids and gases are by volume unless otherwise noted, and all temperatures are given in degrees Celsius.

EXAMPLE I

A. Fusion Partners

I. Human B Lymphocytes

Volunteer patients having cystic fibrosis and screened as having serum titers containing greater than 50 mcg/ml of anti-*P. aeruginosa* serotype-specific antibodies (IgM, IgG ad/or IgA) were identified. Venous blood was drawn in sodium citrate. The blood was centrifuged and the buffy coat was harvested and then gradient centrifuged using Ficoll/Hypaque to separate lymphocytes. T cells were removed by AET-SRBC rosetting. The remaining B cell-enriched lymphocyte population was transformed with Epstein-Barr virus as described by Foung et al., supra, except that cells were cultured at $10^3$–$10^4$ cells per well in 96-well microtiter plates. The wells were initially screened using a commercial multivalent *Pseudomonas aeruginosa* vaccine (obtained from Parke Davis), followed by a bacterial ELISA as described below utilizing Pseudomonas strains from commercial Fisher-Devlin serotypes 1 through 7 (obtained from ATCC, Rockville, Md., and identified further hereinbelow).

II. F3B6 (Mouse×Human Line)

A mouse-human heterohybrid fusion partner designated F3B6 (adapted to 99% serum-free medium and deposited with the ATCC under ATCC Accession No. HB 8785 on Apr. 18, 1985) was constructed by fusing peripheral blood lymphocyte (PBL) B cells obtained from a blood bank with the murine plasmacytoma cell line NS1 obtained from ATCC under ATCC No. TIB18(P3/NS1/1-AG4-1). The PBL cells from random buffy coat were transferred to a 50 ml centrifuge tube and diluted with 30 ml Hanks' balanced salt solution ($Ca^{2+}$-free/$Mg^{2+}$-free) (HBSS—/—). Then 10 ml Ficoll-Hypaque was added and the mixture centrifuged at 1500 rpm for 15 minutes at room temperature. The interface was removed and the mixture was washed with HBSS−/− and resuspended in HBSS−/−. The cells were counted.

The NS-1 cells were grown in 4×T75 flasks and harvested, washed with HBSS−/− and resuspended in HBSS−/−. The cells were counted.

Approximately $5\times10^7$ B-cells and $2.5\times10^7$ NS-1 cells (2:1 ratio) were added to each of 5–50 ml centrifuge tubes for fusion. The mixture was centrifuged at 1200 rpm for eight minutes at room temperature to form a tight pellet. All of the supernatant was removed and the tube was kept at 37° C. for further manipulations. A total of 1 ml of warm 50% polyethyleneglycol of molecular weight 1540 (PEG 1540) (BDH Chemicals, Poole, England) was added over a one minute period using a 1 ml pipette. The cell pellet was gently stirred with the tip of the pipette as the PEG was being added. Then 1 ml of HBSS−/− was added at 37° C. over a one-minute period to dilute gradually the PEG. The cells were washed twice with HBSS−/− and resuspended in Iscove's medium in several T150 flasks.

On day 2 the cell lines were washed in HBSS−/− in 50 ml centrifuge tubes. A total of 10 ml of Ficoll-Hypaque was added to the tubes. The tubes were centrifuged at 1500 rpm for 15 minutes at room temperature and the live cells at the interface were removed. The pellet was washed twice with RPMI-1640 (Gibco) and resuspended in an enriched hypoxanthine/azaserine selection medium (EHA) consisting of 100 PM hypoxanthine (Sigma), 5 μg/ml azaserine (Sigma) and Iscove's medium (Gibco), 10% NCTC (M. A. Biologicals), 20% heat-inactivated-FBS. The density was adjusted to $2.5\times10^4$ cells/ml medium.

At day 5 the suspensions were washed twice with HBSS−/− and resuspended in 10 ml Iscove's medium. Live cells were separated by Ficoll-Hypaque density gradient centrifugation described as above. Cells were washed twice with RPMI-1640+20% FBS, and then plated out in 96-well plates at $10^6$ cells/ml. At days 7, 9 and 12 the EHA selection medium described above was added each time. At days 15 and 18 the plates were fed with EHMT medium containing hypoxanthine, methotrexate and thymidine. The supernatants were assayed for Ig secretion and Ig secreting hybrid cell lines were cloned by limiting dilution in U bottom 96 well plates.

Well F3B6 was selected for 6-thioguanine selection. Several roller bottles of F3B6 were grown up. A total of 10 μg/ml of 6-thioguanine was added to the roller bottles. Dead cells were removed by Ficoll-Hypaque density gradient centrifugation on days 2, 5 and 7. A 6-thioguanine resistant clone was grown up. Test fusions were performed, and the cell line was tested for ouabain resistance.

The resultant cell line was adapted to growth and maintenance in 99% serum-free medium and 1% FBS for more reproducible manufacturing by the following multi-step process:

1. Two days prior to subculturing, the cells were fed with a mixture of the Iscove's DME in which they were growing, 50% of the amount of FBS in the medium in which they were growing, and 50% by weight of serum-free medium HL-1 supplied by Ventrex, Inc.

2. Two days later, or when the hybridoma cells reached densities of $8\times10^5$ to $1\times10^6$ cells/ml, the cells were subcultured and planted with 50% of Iscove's DME medium and 50% of the serum-free medium. The cells were removed from the latter medium by centrifugation at 200×g for five minutes. The Iscove's DME medium was mixed with 50% of the serum-free medium to form a 50:50 mixture, in which the cell pellet was suspended and then counted. An appropriate amount of cell suspension was planted in the vessel with 50% Iscove's DME and 50% serum-free medium. The planted cell densities preferably do not fall below $5\times10^4$ cells/ml and not exceed $1\times10^5$ cells/ml.

3. After two to three days post-planting, or when the cell density reached $8\times10^5$ to $1\times10^6$ cells/ml, the cells were refed with 50% Iscove's DME and 50% serum-free medium.

4. Step 3 was repeated for another passage.

5. After two to three days in culture or when the cell density reached $8\times10^5$ to $1\times10^6$ cells/ml and viability was about 85%, the cells were cultured on serum-free medium only. When the cells were planted in the serum-free medium for the first time the cell densities were between $1\times10^5$ to $8\text{-}9\times10^5$ cells/ml. The final medium was HL1 with 1% FBS.

B. Fusion Protocol

The fusion mixture contained polyethylene glycol (PEG) 4000, 40% (w/v); dimethylsulfoxide (DMSO), 10% (v/v) and 5 μg/ml poly-1-arginine in Hanks' balanced salt solution (HBSS)−/+ ($Ca^{2+}$-free, 2 mM $MgSO_4$). Forty g of PEG 4000 was combined with 10 ml of DMSO and 50 ml of HBSS−/+. The mix was autoclaved for 25 minutes. Before use, the PH of the fusion mixture was adjusted to between 7.5 and 8.5 with sterile 0.1 N NaOH.

Plates (6-well cluster, 35 mm well diameter) were prepared as follows: 2 ml of HBSS−/+ and 50 μl of a filter sterilized, 20–100 μg/ml, peanut agglutinin (PNA, Sigma) were added to each well. Plates were incubated at 37° C. for at least one hour prior to use. PNA stock was stored frozen, and a freshly thawed aliquot was used to coat fusion cells. Smaller sized wells were used if cell numbers were limited.

Parent cells in Ficoll-Hypaque were washed twice in HBSS−/+ at room temperature and subsequently resuspended and combined at a ratio of 5:1 to 1:1 lymphocyte:F3B6 in HBSS−/+ warmed to 37° C. Two ml of the combined cell suspension ($3\times10^7$ cells/well) was added to each pretreated well containing 1 μg/ml PNA coating solution. The wells were incubated at 37° C. for one minute. Plates were spun onto bottom of the plate at 400–500×g, room temperature, for five minutes to form a monolayer of cells. Supernatant was then aspirated off the plates, leaving behind adherent coating of cells.

Two ml of PEG fusion mixture described above and warmed to 37° C. was carefully added down the side of the fusion cell. After one minute, the PEG solution was diluted with a fusion dilution mixture (FDM) of 5% DMSO (Sigma) HBSS−/+ (warmed to 37° C. and filter sterilized) at a rate of 2 ml/min (0.5 ml every 15 sec) for the next two-three min (4–6 ml). For the next two minutes the FDM was added at a rate of 4 ml/min with mixing. FDM was always added down the side of the well, so as not to disturb the monolayer, and the plates were swirled constantly to ensure optimal mixing.

At the end of the two minutes the wells were aspirated to remove diluted PEG fusion mixture. The remaining film of PEG mixture was diluted at a rate of 2 ml/min for one-two min with warm FDM. Again the plate was constantly swirled. Over a period of 0.25–2 minutes with swirling, 5 ml of HBSS−/+ warmed to 37° C. was added to the fusion well at a rate of 1 ml/15 sec. The well was then filled up with HBSS−/+ and all supernatant was aspirated from the monolayer. Finally, each fusion well was washed once or twice with about 5–10 ml of warm HBSS−/+, aspirated and washed again with about 5 ml of HBSS−/+ and aspirated. Five ml of warm Iscove's complete medium and 15–20% FBS, were added to each well, and the plates were incubated at 37° C. for 24 hours. The day following fusion the cells were resuspended at a density of $10^5$ cells/ml in EHA medium containing azaserine (2 μg/ml), hypoxanthine (100 μM), and ouabain (1 μM) and plated at 0.1 ml/well in 96-well plates. Cultures were subsequently fed every three days. Growing hybrids were visible within 10 to 21 days.

C. ELISAs

I. Bacteria

Fifty-100 μl of 5–1.0% glutaraldehyde (Sigma) in deionized water was coated onto flat/bottom microtiter plates (Dynatech). After one to four hours of incubation at room temperature the wells were aspirated or washed twice with distilled water. The bacteria were washed in saline and reconstituted to 0.25% (v/v). Sixty-100 μl of this bacterial suspension was added per well and the plates were spun for 20 minutes at 2000 rpm. The suspensions were incubated overnight or for a minimum of two hours. The plates were then washed with 100 μl phosphate buffered saline containing 0.1 g/liter $MgSO_4$ and 0.1 g/liter, $CaCl_2$ (PBS++), 0.05% Tween 20 surfactant (Sigma), and preferably 0.01% thimerosal and 1% bovine serum albumin (BSA) (Sigma). The supernatant was incubated for 90 minutes at room temperature and washed three times with PBS++, Tween 20 and thimerosal. Then the plate bottom was optionally blotted with soft tissue. Fifty-100 μl of horseradish peroxidase-conjugated goat anti-human IgG (Tago, Inc.) or horseradish peroxidase-conjugated goat anti-human IgM (Jackson Labs) was then added to each well. The wells were incubated at room temperature or 40° C. for 30 minutes and washed up to five times with PBS++, 0.05% Tween 20 and 0.01% thimerosal, and optionally blotted. Two-hundred μl of ABTS substrate was then added to each well, the substrate consisting of 55 mg/ml of ABTS aqueous stock solution diluted 1:1000 with 0.1 M sodium citrate buffer at pH 4.5 to which 1:1000 of 30% $H_2O_2$ was added immediately before use. Each well was incubated for 30 minutes at 37° C. in the dark. The contents of the wells were transferred to a transparent plate and were read with an ELISA reader at 405 nm. Readings were reported on a scale of 1 to 10 with 1=0.0 OD, 10=2.0 OD.

II. LPS

Flat-bottom microtiter plates were coated overnight with 50 μl of a preparation of sonicated LPS, 50 μg/ml in 0.05 mM sodium bicarbonate buffer, pH 9.6. Plates were washed with PBS++ with 0.05% Tween 20 (Sigma), and preferably 0.01% thimerosal up to five times by immersion or with an automated plate washer. Subsequently, 100 μl of of PBS++, 1% BSA, 0.05% Tween 20, and preferably 0.01% thimerosal was added to each well, followed by 100 μl of the test supernatants. Supernatants were incubated for 30 minutes at 4° C. to room temperature and then washed up to five times with the PBS++/Tween/thimerosal mixture. Then a total of 50–100 μl of peroxidase-conjugated goat anti-human IgM (Tago) diluted in PBS++, BSA, Tween 20 and thimerosal was added and the mixture incubated for 30 minutes at room temperature or 40° C. and washed up to five times. Then 200 μl of the ABTS peroxidase substrate described for the bacterial ELISA was added to each well and each well was incubated for 30 minutes at 37° C. in the dark. The contents of the wells were read on a plate ELISA reader at 405 nm.

III. IgM

Immulon II flat-bottom microtiter plates were coated at 100 μl/well with goat anti-human IgM (Tago) diluted 1:100 in 50 mM bicarbonate buffer (pH 9.6). After 90 minutes at 37° C., plates were washed with PBS++, 0.05% Tween 20, and preferably 0.01% thimerosal up to five times by immersion or with automated plate washer. Then 100 μl of PBS++, 1% BSA, 0.05% Tween 20, 0.01% thimerosal was preferably added to each well. A total of 100 μl of test supernatant was added to first wells and preferably duplicate two-fold dilutions were made. One well was preferably left as control. The plates were incubated for 30 minutes at 22° C. and then washed up to five times as described above. Then, a total of 50–100 μl of peroxidase-conjugated goat anti-human IgM antibody (Tago) diluted in PBS++, BSA, Tween 20 and thimerosal was added and the mixture incubated for 30 minutes at room temperature or 40° C and washed up to five times. Then a total of 200 μl of the ABTS peroxidase substrate described for the bacterial ELISA was added to each well. The mixture was incubated for 30 minutes at 37° C. in the dark and read on an ELISA plate reader ($OD_{405}$) using as IgM standard pooled human myeloma (Cappell) previously standardized versus a Tago Standard.

D. Hybrid Screening (B Lymphocyte×F3B6)

Culture supernatants were assayed by bacterial ELISA as described above using bacteria from each serotype of *Pseudomonas aeruginosa* (obtained from ATCC). Positive wells were subcloned and reassayed approximately two weeks later.

Two hybrids, designated CF6 (recognizing only Type 4 *P. aeruginosa*) and L114 (recognizing serotypes 3 and 7), were chosen based on their titers of antibodies against specific serotypes for expansion and further testing.

These hybridomas maintained monoclonal antibody production in continuous culture for at least eight months and secreted 5–10 micrograms of antibody per ml of culture media. The results of whole bacterial ELISA of the antibodies from these hybrids against respective serotypes are reported in Table I.

The antibodies derived from hybrid CF6 were found to be specific to only one serotype whereas the antibodies derived from L114 are specific to more than one serotype.

TABLE I

| | *Pseudomonas aeruginosa* Bacterial ELISA | | | | | | |
|---|---|---|---|---|---|---|---|
| ATCC # Serotype | 27312 (type 1) | 27313 (type 2) | 27314 (type 3) | 27315 (type 4) | 27316 (type 5) | 27317 (type 6) | 27318 (type 7) |
| CF6 | 0* | 0 | 0 | + | 0 | 0 | 0 |
| L114 | 0 | 0 | + | 0 | 0 | 0 | + |

*Magnitude of numbers indicates the degree of monoclonal antibody binding. 0 is negative.
+ is off-scale with the plate reader set at 2.0 absorbance full scale.

The cell lines were routinely recloned every few months using limiting-dilution or soft agar cloning to maintain high secreting heterohybrids. Limiting-dilution (0.3 cells per well) cloning was performed in 96-well U-bottom plates (Costar) in Iscove's DME medium with 20% FBS. Soft agar cloning was performed by placing 1000 cells in 1 ml of 0.33% SeaPlaque agarose (FMC, Rockland, Me.) made in Iscove's DME medium/20% FBS over a bed of 4 ml of SeaKem agarose (0.4%) in 60 mm culture dishes (Falcon). For selection of high producer hybrids, an antigen-specific plaque technique and a non-specific Ig reverse-plaque technique were both useful. For reverse-plaque, Protein A-coated sheep erythrocytes (1.0%) were added to the upper layer of soft agar according to the method of Gronowicz et al., *PNAS* (USA), 6, 588–590 (1976).

The two monoclonal antibodies were tested for binding to electrophoresed lipopolysaccharide. Immunoblots conducted essentially by the procedures of Wang and Larrick, "Immunoblotting", in *Human Hybridomas and Monoclonal Antibodies,* Engelman et al., Plenum:-New York, 1985, demonstrated specific binding of the monoclonal antibodies to the LPS corresponding to the bacterial binding, i.e., CF6 bound only type 4 LPS and L114 recognized a shared determinant between types 3 and 7.

The two human monoclonal antibodies described above were isotyped and found to be IgMs. A sample of the trioma which produces the antibody of serotype 4, which recognizes only one serotype, was deposited at the American Type Culture Collection (ATCC), 12301 Parklawn Drive, Rockville, Md., USA. Deposit dates and accession numbers are given below for this trioma and for the mouse×human fusion partner (adapted to 99% serum-free medium) used to prepare it (F3B6).

| Cell Line | Deposit Date | Accession No. |
|---|---|---|
| CF-6 | 12 March 1985 | HB 8749 |
| F3B6 | 18 April 1985 | HB 8785 |

The deposits above were made pursuant to a contract between the ATCC and the assignee of this patent application, Cetus Corporation. The contract with ATCC provides for permanent availability of the progeny of these cell lines to the public on the issuance of the U.S. patent describing and identifying the deposit or the publications or upon the laying open to the public of any U.S. or foreign patent application, whichever comes first, and for availability of the progeny of these cell lines to one determined by the U.S. Commissioner of Patents and Trademarks to be entitled thereto according to 35 USC § 122 and the Commissioner's rules pursuant thereto (including 37 CFR §1.14 with particular reference to 886 OG 638). The assignee of the present application has agreed that if the cell lines on deposit should die or be lost or destroyed when cultivated under suitable conditions, it will be promptly replaced on notification with a viable culture of the same cell lines.

Modifications of the above-described modes for carrying out the invention that are obvious to those of skill in the fields of hybridoma technology, immunology, bacterial infections, and related fields, are intended to be within the scope of the following claims.

What is claimed is:

1. A human anti-Pseudomonas monoclonal antibody which binds specifically to at least one of serotypes 1, 2, 3, 4, 5, 6 or 7 of *Pseudomonas aeruginosa.*

2. The antibody of claim 1 which is of the isotype IgM.

3. The antibody of claim 1 which binds to serotypes 3 and 7 of *Pseudomonas aeruginosa.*

4. The antibody of claim 1 which binds to serotype 4 of *Pseudomonas aeruginosa.*

5. A cell line which is a fusion product of an immortal cell line and a cell line which produces a human anti-Pseudomonas monoclonal antibody which binds specifically to at least one of serotypes 1, 2, 3, 4, 5, 6, or 7 of *Pseudomonas aeruginosa,* wherein said fusion product remains viable for at least six months and is able to produce the antibody through at least about 50 passages.

* * * * *